United States Patent [19]
Rozga et al.

[11] Patent Number: 5,993,406
[45] Date of Patent: Nov. 30, 1999

[54] ARTIFICIAL GUT

[75] Inventors: Jacek Rozga, Westlake Village; Achilles A. Demetriou, Bel Aier, both of Calif.

[73] Assignee: Cedars-Sinai Medical Center, Los Angeles, Calif.

[21] Appl. No.: 08/856,522

[22] Filed: May 14, 1997

[51] Int. Cl.$^6$ .................................................. A61M 35/00
[52] U.S. Cl. ........................................................... 604/4
[58] Field of Search ..................................... 604/4–6, 173, 604/93; 623/11, 12; 435/283–285

[56]  References Cited

U.S. PATENT DOCUMENTS

| | | |
|---|---|---|
| 4,241,187 | 12/1980 | White . |
| 4,643,715 | 2/1987 | Isono et al. . |
| 5,011,472 | 4/1991 | Aebischer et al. . |
| 5,015,585 | 5/1991 | Robinson . |
| 5,043,260 | 8/1991 | Jauregui . |
| 5,055,198 | 10/1991 | Shettigar . |
| 5,116,494 | 5/1992 | Chick et al. . |
| 5,152,743 | 10/1992 | Gorsuch et al. . |
| 5,263,982 | 11/1993 | Shimomura et al. . |
| 5,270,192 | 12/1993 | Li et al. . |
| 5,368,555 | 11/1994 | Sussman et al. . |
| 5,387,237 | 2/1995 | Fournier et al. . |
| 5,525,305 | 6/1996 | Minekus et al. . |

FOREIGN PATENT DOCUMENTS

| | | |
|---|---|---|
| WO 86 02378 | 4/1986 | WIPO . |
| WO 91 00119 | 1/1991 | WIPO . |
| WO 92 07615 | 5/1992 | WIPO . |
| WO 95 21911 | 8/1995 | WIPO . |

OTHER PUBLICATIONS

Hidalgo, I. J. et al: "Characterization of the Unstirred Water Layer in Caco–2 Cell Monolayers Using a Novel Diffusion Apparatus", Pharmaceutical Research, vol. 8, No. 2, Feb. 1991, pp. 222–227, XP000613852.

Quaroni, A. et al: "Development of Intestinal Cell Cultrure Models for Drug Transport and Metabolism Studies" ADV Drug Delivery Rev; Advanced Drug Delivery Reviews Nov. 15, 1996, Elsevier Science B. V., Amsterdam, Netherlands, vol. 22, No. 1–2, Nov. 15, 1996, pp. 3–52, XP002076583.

Grass, George M: "Simulation Models to Predict Oral Drug Absorption From In Vitro Data" ADV Drug Delivery Rev; Advanced Drug Delivery Reviews January 15, 1997 Elsevier Science B.V., Amsterdam, Netherlands, vol. 23, No. 1–3, Jan. 15, 1997, pp. 199–219, XP002076584.

*Primary Examiner*—John G. Weiss
*Assistant Examiner*—Ki Yong O
*Attorney, Agent, or Firm*—Pretty, Schroeder & Poplawski

[57] ABSTRACT

An artificial gut (100) comprises a first hollow fiber (203) having an inner surface (215) that is lined with at least a portion of a layer of one or more of a plurality of biological components (205) that typically line a mammalian gut. Further, a second hollow fiber (201) is adjacent the first hollow fiber. The layer of one or more of the plurality of biological components can consist essentially of enterocytes. The enterocyte-lined inner surface is perfused with a feeding solution containing nutrients, and the enterocytes absorb, process, and transport the nutrients across the wall of the first hollow fiber. The nutrients eventually diffuse into the second hollow fiber. A perfusate selected from the group consisting of culture medium, blood, and plasma, can perfuse an inner surface of the second hollow fiber, whereby the perfusate is nourished by the nutrients.

9 Claims, 1 Drawing Sheet

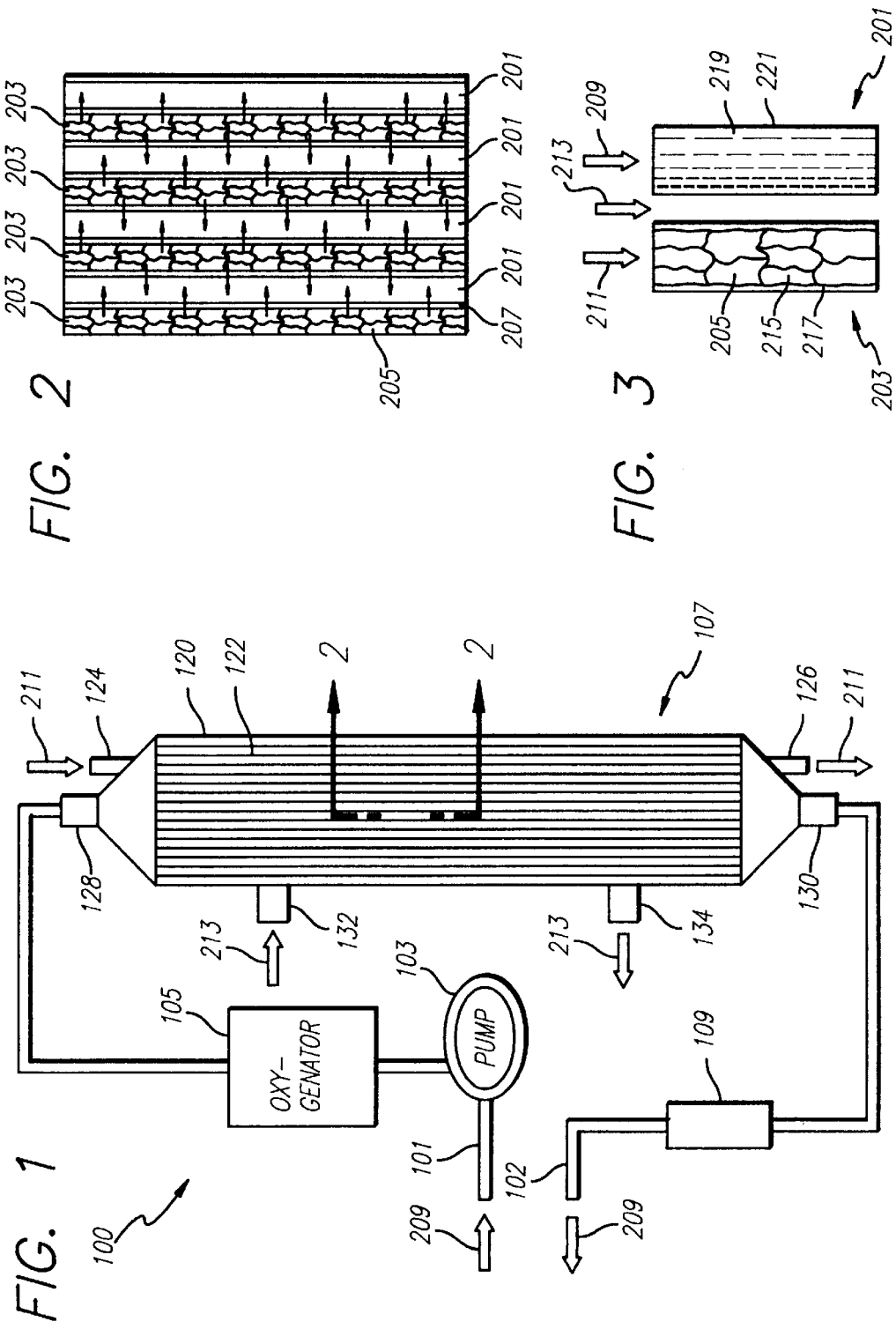

ARTIFICIAL GUT

FIELD OF THE INVENTION

The present invention relates generally to the field of artificial organs, and more particularly to an artificial gut and method therefore.

BACKGROUND OF THE INVENTION

In the medical environment, it is often desirable to have apparatus that mimic human organs. Such apparatus can be used, for example, to study the organ and its reaction to agents, to produce cells, tissues, or other materials, or to treat patients whose human organ is failing.

Artificial organs, such as, kidney, liver, lung, and pancreas, have been described in the art. Furthermore, a model of a digestive tract that simulates peristaltic movements that move the contents of the intestine onward has been described. There is not known, however, an artificial gut that adequately mimics the anatomy, morphology, and function of the mammalian small intestine, especially the absorption of nutrients from the contents of the intestine into the blood stream.

A need therefore exists for an artificial gut, and a method of manufacture and use therefore, that mimics the anatomy, morphology, and function of the mammalian small intestine.

SUMMARY OF THE INVENTION

The artificial gut, and method of manufacture and use therefore, described herein provides advantages over a mechanical gut in that it tends to mimic the anatomy, morphology, and function of the mammalian small intestine.

According to the present invention, the foregoing advantages are principally provided by an artificial gut that comprises a first hollow fiber having an inner surface that is lined with at least a portion of a layer of one or more of a plurality of biological components that typically line a mammalian gut. Further, a second hollow fiber is adjacent to the first hollow fiber.

In accordance with another aspect of the invention, the layer of one or more of the plurality of biological components consists essentially of enterocytes. The enterocyte-lined inner surface is perfused with a feeding solution containing nutrients, and the enterocytes absorb, process, and transport the nutrients across the wall of the first hollow fiber. The nutrients eventually diffuse into the second hollow fiber. A perfusate selected from the group consisting of culture medium, blood, and plasma, can perfuse an inner surface of the second hollow fiber, whereby the perfusate is nourished by the nutrients.

In another aspect of the invention, there can be a first system of a plurality of hollow fibers and a second system of a plurality of hollow fibers contained in a housing. The housing and outer surfaces of the first system of hollow fibers and the second system of hollow fibers define an extra-fiber space. The housing includes a first set of perfusion ports coupled with the first system of hollow fibers, and a second set of perfusion ports coupled with the second system of hollow fibers.

According to another aspect of the invention, the enterocytes lining the first system of hollow fibers absorb the nutrients and pass them into the extra-fiber space. The nutrients in the extra-fiber space then diffuse into the second system of hollow fibers.

In accordance with the method of manufacture of this invention, providing a first system of a plurality of hollow, porous fibers and a second system of a plurality of hollow, porous fibers, and lining the inner surface of each of the plurality of hollow, porous fibers of the first system with a layer of one or more of a plurality of biological components that line a mammalian gut.

In accordance with the method of using of this invention, providing an artificial gut including a first system of a plurality of hollow fibers and a second system of a plurality of hollow fibers, and lining the inner surface of each of the plurality of hollow fibers of the first system with a layer of one or more of the plurality of biological components. The lined inner surface of each of the plurality of hollow fibers of the first system is perfused with a first perfusate, and the inner surface of each of the plurality of hollow fibers of the second system is perfused with a second perfusate.

The method more particularly comprises the substeps of seeding the first system of a plurality of hollow fibers with the one or more of the plurality of biological components, and perfusing the outer surface of each of the plurality of hollow fibers of the first system with an oxygenated cell culture media enriched with humoral components. The humoral components maintain viability and morphological integrity of the plurality of the biological components, and facilitate or enhance their function.

Additional advantages and novel features of the invention will be set forth in part in the description which follows, wherein only the preferred embodiments of the invention are shown and described, and in part become apparent to those skilled in the art upon examination of the following detailed description or may be learned by practice of the invention. The advantages of the invention may be realized and attained by means of the instrumentalities and combinations particularly pointed out in the appended claims.

BRIEF DESCRIPTION OF THE DRAWINGS

FIG. 1 is an elevation view of an artificial gut.

FIG. 2 is an enlarged, partial sectional view of a bioreactor along plane 2'—2'.

FIG. 3 is a detailed, sectional view of a first hollow fiber and a second hollow fiber.

DESCRIPTION OF THE PREFERRED EMBODIMENTS

Reference will now be made in detail to the embodiments configured according to the present invention.

FIG. 1 is an elevation view of an artificial gut 100 for mimicking a mammalian gut. Artificial gut 100 comprises a bioreactor 107 that includes a rigid plastic housing 120 containing a first system of hollow fibers and a second system of hollow fibers.

As shown in FIG. 2, which is an enlarged, partial sectional view of bioreactor 107 along plane 2'—2', the first system of hollow fibers includes a plurality of first hollow fibers 203, and the second system of hollow fibers includes a plurality of second hollow fibers 201. The plurality of first hollow fibers 203 the plurality of second hollow fibers 201 are adjacent and intertwined with each other.

FIG. 3 is a detailed, sectional view of first hollow fiber 203 and second hollow fiber 201. First hollow fiber 203 has an inner surface 215 and an outer surface 217. Likewise, second hollow fiber 201 has an inner surface 219 and an outer surface 221. Housing 120 and outer surfaces 221,217 of the plurality of first and second hollow fibers 201,203 define an extra-fiber space 207.

The inner surfaces 215 define a first compartment that is separate from extra-fiber space 207. Likewise, the inner surfaces 219 define a second compartment that also is separated from extra-fiber space, or third compartment, 207. Additionally, the first compartment and the second compartment are separated from each other.

The mammalian gut is typically lined with a plurality of biological components, for example, enterocytes, crypt cells, basement membrane, and matrix components. A layer of one or more of the plurality of biological components 205 lines at least a portion of inner surface 215 of first hollow fiber 203.

Referring back to FIG. 1, housing 120 further includes a first set of perfusion ports-inlet port 124 and outlet port 126-coupled with the first system of hollow fibers. The first set of perfusion ports admit a first perfusate 211 through inlet port 124, which perfuses the lined inner surfaces 215 of first hollow fibers 203. First perfusate 211 exits outlet port 126. First perfusate 211 is transparent in FIGS. 2 and 3.

Housing 120 further includes a second set of perfusion ports-inlet port 128 and outlet port 130-coupled with the second system of hollow fibers. The second set of perfusion ports admit a second perfusate 209 through inlet port 128, which perfuses the inner surfaces 219 of second hollow fibers 201. Second perfusate 211 exits outlet port 130.

Housing 120 further includes a third set of perfusion ports-inlet port 132 and outlet port 134-coupled with extra-fiber space 207. The third set of perfusion ports admit a third perfusate 213 through inlet port 132, which perfuses at least the outer surfaces 217 of the first hollow fibers 203. The third perfusate exits outlet port 134.

Artificial gut 100 further comprises a pump 103 that circulates second perfusate 209 through the second system of hollow fibers via the second set of ports; an oxygenator 105, coupled between the pump and the second system of hollow fibers, that enriches the second perfusate 209 with oxygen before it enters the second system of hollow fibers via inlet port 128; and, finally, a microporous filter 109 that filters out the one or more biological components from second perfusate 209 after second perfusate 209 leaves the second system of hollow fibers via outlet port 130. The filtering prevents leakage of the biological component into, for example, a patient's blood circulation when a patient is connected to lines 101,102.

In the preferred embodiment, first perfusate 211 consists essentially of a feeding solution including nutrients. The feeding solution can be, for example, a liquid food formula or a test substance. Further, second perfusate 209 is selected from the group consisting of culture medium, blood, and plasma. And, third perfusate 213 consists essentially of a warm (37° C.) oxygenated cell culture media enriched with humoral components, for example, nutrients, hormones, or trophic/growth factors, which are normally present in the animal or human intestinal lumen or in the blood that nourishes the intestinal wall.

Also in the preferred embodiment, first hollow fibers 203 have large pores, and second hollow fibers 203 have pores sized to a predetermined molecular weight cut-off at or below the level of the largest molecules absorbed in the mammalian gut during the normal process of digestion. Furthermore, inner surfaces 215 are lined with a confluent layer of one or more biological components 205, for example, enterocytes.

The method of operation of artificial gut 100 constructed as described above will be now be described.

One or more of the plurality of biological components is harvested from the mammalian intestine or a biological component cell line, and the harvested one or more of the biological components is used to seed the first system of hollow fibers. The technique for harvesting and seeding the biological components is well known in the art.

The harvested biological components are then grown in bioreactor 107 by perfusing outer surfaces 217 of first hollow fibers 203 with third perfusate 213 via the third set of ports. The one or more biological components grow and eventually line inner surfaces 215 of first hollow fibers 203 with a layer of the seeded biological components.

Prior to normal operation of artificial gut 100 and during the process of seeding, growing, or maintaining the one or more of the biological components, outer surface 217 of first hollow fibers 203 is continuously perfused with third perfusate 213. Perfusing with the third perfusate maintains the viability, integrity, and function of the one or more biological components lining inner surfaces 215 of first hollow fibers 203.

Prior to normal operation, third perfusate 213 is vacated from extra-fiber space 207 via outlet port 134.

In normal operation, lined inner surface 215 of first hollow fiber 203 is perfused with first perfusate 211, and inner surface 219 of second hollow fiber 201 is perfused with second perfusate 209. Extra-fiber space 207 is filled with a mixture of diffused products from first perfusate 211 and second perfusate 209 that migrate through first and second hollow fibers 203,201.

In the preferred embodiment, enterocytes 205 absorb the nutrients from feeding solution 211. The nutrients are then processed and passed into extra-fiber space 207 by enterocytes 205; and, ultimately, the nutrients pass into second hollow fiber 201 where they are absorbed by either the culture medium, blood, or plasma 209. The arrows shown in FIG. 2 indicate the transport of nutrients across the enterocyte layer into the lumen of fibers 201.

Those skilled in the art will recognize that various modifications and variations can be made in the artificial gut of the present invention and in construction and operation of this artificial gut without departing from the scope or spirit of this invention. For example, one of ordinary skill in the art will appreciate that potential applications of the artificial gut include but are not limited to (a) study of the pathophysiology of the intestinal tract, (b) study of the absorption of nutrients and other agents, (c) testing of new enteral/parenteral nutrition formulas and studying their effect on artificial gut morphology and function, (d) an ex vivo system to feed human patients with short-gut syndrome, malabsorption of various etiology, and surgical patients requiring nutritional support, and (e) use of a device as an alternative to intravenous total parenteral nutrition.

What is claimed is:

1. A method of using a gut that mimics a mammalian gut that is lined with a plurality of biological components, the method comprising the steps of:

providing an artificial gut including,
a first system of a plurality of hollow fibers, each of the plurality of hollow fibers of the first system has an inner surface and an outer surface, and
a second system of a plurality of hollow fibers, each of the plurality of hollow fibers of the second system has an inner surface and an outer surface;

lining the inner surface of each of the plurality of hollow fibers of the first system with a layer of one or more of the plurality of biological components;

perfusing the lined inner surface of each of the plurality of hollow fibers of the first system with a first perfusate; and perfusing the inner surface of each of the plurality of hollow fibers of the second system with a second perfusate.

2. The method of claim 1 wherein the step of lining the inner surface of each of the plurality of hollow fibers of the first system with a layer of one or more of a plurality of biological components includes the substeps of:

seeding the first system of a plurality of hollow fibers with the one or more of the plurality of biological components; and perfusing the outer surface of each of the plurality of hollow fibers of the first system with a third perfusate.

3. The method of claim 2 wherein the third perfusate consists essentially of an oxygenated cell culture media enriched with hormonal components.

4. The method of claim 3 wherein the first perfusate consists essentially of a feeding solution including nutrients.

5. The method of claim 4 wherein the one or more of the plurality of biological components consists essentially of enterocytes, the method further comprising the steps of absorbing the nutrients and passing them into the extra-fiber space.

6. The method of claim 5 further comprising the step of diffusing the nutrients passed into the extra-fiber space into the second system of a plurality of hollow fibers.

7. The method of claim 6 wherein the second perfusate is selected from the group consisting of culture medium, blood, and plasma.

8. The method of claim 7 further comprising the step of enriching the second perfusate with oxygen before it enters the second system of a plurality of hollow fibers.

9. The method of claim 8 further comprising the step of a filtering the second perfusate after it exits the second system of a plurality of hollow fibers.

* * * * *

UNITED STATES PATENT AND TRADEMARK OFFICE
CERTIFICATE OF CORRECTION

PATENT NO. : 5,993,406
DATED : November 30, 1999
INVENTOR(S) : Rozga, Jacek, et al.

It is certified that error appears in the above-identified patent and that said Letters Patent is hereby corrected as shown below:

In the "Inventors" field on the cover sheet, delete "Bel Aier" and insert --Bel Air--.

In claim 4, line 1, delete "3" and insert --1--.

Signed and Sealed this

Fourteenth Day of November, 2000

Attest:

Q. TODD DICKINSON

*Attesting Officer*            *Director of Patents and Trademarks*